United States Patent [19]
Burke et al.

[11] Patent Number: 5,693,318
[45] Date of Patent: Dec. 2, 1997

[54] STABLE SALICYLIC ACID AND PEROXIDE CONTAINING SKIN AND HAIR CLEANSER COMPOSITION

[75] Inventors: John Jerome Burke, Sparta, N.J.; Joanne Paula Gorczyca, Livonia, Mich.

[73] Assignee: BASF Corporation, Mount Olive, N.J.

[21] Appl. No.: 680,085

[22] Filed: Jul. 15, 1996

[51] Int. Cl.⁶ .................................................. C11D 17/00
[52] U.S. Cl. ...................... 424/78.02; 514/828; 514/846; 558/104
[58] Field of Search ........................... 558/104; 252/89.1; 424/78.02, 70.22, 70.23; 514/828, 846

[56] References Cited

U.S. PATENT DOCUMENTS

| | | | |
|---|---|---|---|
| 4,623,743 | 11/1986 | Kurosaki et al. | 558/105 |
| 4,904,405 | 2/1990 | Kajihara et al. | 252/90 |
| 5,124,077 | 6/1992 | Kajihara et al. | 252/545 |

FOREIGN PATENT DOCUMENTS

| | | |
|---|---|---|
| 0 191 214 | 7/1991 | European Pat. Off. . |
| 2242686 | 3/1990 | Japan . |
| 04108724A | 8/1990 | Japan . |
| 04249596A | 12/1990 | Japan . |
| 05001081A | 6/1991 | Japan . |
| 05009495A | 7/1991 | Japan . |
| 05009497A | 7/1991 | Japan . |

*Primary Examiner*—Terressa Mosley
*Attorney, Agent, or Firm*—Joanne P. Will

[57] ABSTRACT

The present invention relates to the use of phosphate esters for the improvement of water solubility of salicylic acid and stability of peroxide compounds in an aqueous cleanser.

8 Claims, No Drawings

STABLE SALICYLIC ACID AND PEROXIDE CONTAINING SKIN AND HAIR CLEANSER COMPOSITION

FIELD OF THE INVENTION

The present invention relates to an aqueous skin and hair cleanser composition comprising peroxides, salicylic acid, and phosphate esters. The aqueous skin cleanser composition is unique in that it allows the incorporation of salicylic acid and also provides a stable environment for the peroxides.

BACKGROUND OF THE INVENTION

The use of peroxides, for example, hydrogen peroxide and salicylic acid for their benefits to human health is a familiar concept to those concerned with human hygiene and to consumers alike. Specifically, *The Merck Index*, Eleventh Edition, 1989 lists the therapeutic uses of hydrogen peroxide as an antiinfective/topical antiseptic. Salicylic acid is described as a keratolytic. Recent oral care compositions containing hydrogen peroxide have been developed for general consumer use. Additionally, salicylic acid based skin creams are available for general consumer use. However, aqueous based skin and hair care compositions containing both peroxide compounds and salicylic acid are not available. Such a skin and hair care composition would be welcomed by the consumer because it would combine the utility of an antiseptic and a keratolytic agent, leaving the skin and hair both disinfected and refreshed.

However, formulating aqueous skin and hair care compositions with peroxides and salicylic acid presents several problems because of the properties of the peroxides and salicylic acid. Specifically, peroxides are such strong oxidizers that they can be used topically only after dilution. Moreover, dilution with water will accelerate their decomposition, especially if the water contains even the smallest concentration of impurities such as metals, metal ions, and metal salts. Peroxides are therefore difficult to process without compromising their activity. Further, due to their reactivity, costly passivated equipment (equipment cleaned and treated with acid solutions so that the metal ions are stripped away) and ultrapure water (considerably more costly than deionized) must be used in producing peroxide containing compositions. This ultimately adds to the cost of the products.

Regarding salicylic acid, it is not very soluble in water, even at low use concentrations. It is somewhat more soluble in hot water but hot water seriously compromises the peroxide compound stability. Clearly, there is an unfulfilled need in the art for stable skin care compositions comprising peroxides and salicylic acid.

Applicants studied the problem of formulating peroxides and salicylic acid containing compositions and theorized that phosphate esters might be useful in stabilizing peroxides and salicylic acid containing compositions. Phosphate esters are known to those skilled in the art as being useful in skin and hair cleansing compositions. Specifically, U.S. Pat. No. 5,124,077, U.S. Pat. No. 4,623,743, and U.S. Pat. No. 4,904,405, disclose the use of phosphate ester surfactants to impart mildness and to cleanse the skin and hair. Japanese Abstracts, 05009497A (JP), 05001081A (JP), 04108724A (JP), 05009495A (JP), 04249596A (JP), 2242686A (JP) also disclose the use of specific phosphate ester surfactants to impart mildness and cleansing of skin and hair. The focus of these disclosures is also on good foaming of the finished formulation. Some of these disclosures center around the synthesis of glucose or other sugar-based phosphate esters to take maximum advantage of skin mildness. Others show the advantage of the synthesis of trialkylammonium phosphate esters for skin and hair conditioning. However, none of these references describe the use of phosphate esters for improving the solubility and stability of peroxide compounds/salicylic acid containing skin care compositions.

Finally, DE 3583936 (EP 0191214B1) discloses a blemish treatment composition comprising: 0.1–6.10 g boric acid, 0.01–1.6 ml ammonium hydroxide, 0.02–1.2 g camphora, and 0.07–1.1 ml hydrogen peroxide.

Applicants have surprisingly discovered that use of phosphate esters facilitates the formulating of an aqueous based skin cleanser that is compatible with and stabilizes peroxides and salicylic acid. Further, the compositions of the present invention be prepared in unpassivated equipment and with standard deionized water which reduces the production costs as compared to preparation in passivated equipment and ultra pure water.

Finally, the skin care composition of the present invention is aesthetically pleasing to the user and is easily dispensed from a mechanical pump, aerosol or a tube.

SUMMARY OF THE INVENTION

An aqueous skin care composition comprising:

a. 0.5 to 5% peroxides;

b. 0.5 to 5% salicylic acid;

c. 0.1 to 50% adjunct surfactant;

d. 0.1 to 5% phosphate ester, selected from one of the following 4 structures or mixtures thereof:

Formula I

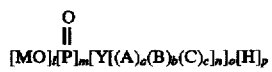

wherein l=0–2.9, m=0.1–1, n=1, o=1–3, p=0–0.9, A, B and C are ethylene oxide, propylene oxide, butylene oxide, tetramethylene oxide and mixtures thereof; a=0–30, b=0–30, c=0–30, M is H, alkali metal, or mixtures thereof; Y is a saturated or unsaturated, linear or branched ,cyclic or acyclic, substituted or unsubstituted alcohol having from 1 to 30 carbon atoms;

or

Formula II

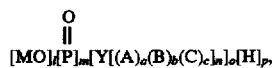

wherein l=0–5.9, m=0.1–2, n=2, o=0.1–6, p=0–1.9, A, B and C are ethylene oxide, propylene oxide, butylene oxide, tetramethylene oxide and mixtures thereof; a=15–100, b=10–250, c=0–100, M is H, alkali metal, or mixtures thereof; Y is a diol having from 2 to 30 carbon atoms, linear or branched, including but not limited to ethylene glycol, diethylene glycol, propylene glycol, and 1,10-decane diol or Y is an alkyl, aryl or alkylaryl primary amine including but not limited to tallow amine or aniline;

or

Formula III

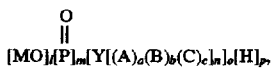

wherein $l=0-8.9$, $m=0.1-3$, $n=3$, $o=0.1-9$, $p=0-2.9$, A, B and C are ethylene oxide, propylene oxide, butylene oxide, tetramethylene oxide and mixtures thereof; $a=15-120$, $b=10-350$, $c=100$, M is H, alkali metal, or mixtures thereof; Y is the residue of an organic compound having three reactive hydrogens which are attached to oxygen, nitrogen or sulfur atoms and mixtures thereof;

or

Formula IV

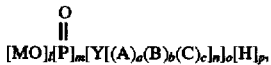

wherein $l=0-11.9$, $m=0.1-4$, $n=4$, $o=0.1-12$, $p=0-3.9$, A, B and G are ethylene oxide, propylene oxide, butylene oxide, tetramethylene oxide and mixtures thereof; $a=15-150$, $b=20-500$, $c=0-150$, M is H, alkali metal, or mixtures thereof; Y is a tetrafunctional initiator containing reactive hydrogens attached to oxygen, nitrogen or sulfur atoms and mixtures thereof.

Each phosphate ester is a mixture of mono-, di- and tri-esters. The mixture is predominately mono-ester.

DETAILED DESCRIPTION OF THE INVENTION

An aqueous skin care composition comprising:

a. 0.5 to 5% peroxides;

b. 0.5 to 5% salicylic acid;

c. 0.1 to 50% adjunct surfactant;

d. 0.1 to 5% phosphate ester, selected from one of the following 4 structures or mixtures thereof:

Formula I

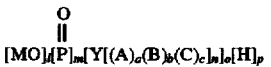

wherein $l=0-2.9$, $m=0.1-1$, $n=1$, $o=0.1-3$, $p=0-0.9$, A, B and C are ethylene oxide, propylene oxide, butylene oxide, tetramethylene oxide and mixtures thereof; $a=0-30$, $b=0-30$, $c=0-30$, M is H, alkali, metal, or mixtures thereof; Y is a saturated or unsaturated, linear or branched, cyclic or acyclic, substituted or unsubstituted alcohol having from 1 to 30 carbon atoms;

or

Formula II

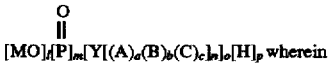 wherein wherein $l=0-5.9$, $m=0.1-2$, $n=2$, $o=0.1-6$, $p=0-1.9$, A, B and C are ethylene oxide, propylene oxide, butylene oxide, tetramethylene oxide and mixtures thereof; $a=15-100$, $b=10-250$, $c=0-100$, M is H, alkali metal, or mixtures thereof; Y is a diol having from 2 to 30 carbon atoms, linear or branched, including but not limited to ethylene glycol, diethylene glycol, propylene glycol, and 1,10-decane diol or Y is an alkyl, aryl or alkylaryl primary amine including but not limited to tallow amine or aniline;

or

Formula III

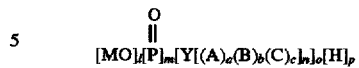

wherein $l=0-8.9$, $m=0.1-3$, $n=3$, $o=0.1-9$, $p=0-2.9$, A, B and C are ethylene oxide, propylene oxide, butylene oxide, tetramethylene oxide and mixtures thereof; $a=15-120$, $b=10-350$, $c=100$, M is H, alkali metal, or mixtures thereof; Y is the residue of an organic compound having three reactive hydrogens which are attached to oxygen, nitrogen or sulfur atoms and mixtures thereof;

or

Formula IV

wherein $l=0-11.9$, $m=0.1-4$, $n=4$, $o=0.1-12$, $p=0-3.9$, A, B and C are ethylene oxide, propylene oxide, butylene oxide, tetramethylene oxide and mixtures thereof; $a=15-150$, $b=20-500$, $c=0-150$, M is H, alkali metal, or mixtures thereof; Y is a tetrafunctional initiator containing reactive hydrogens attached to oxygen, nitrogen or sulfur atoms and mixtures thereof.

Each phosphate ester is a mixture of mono-, di- and tri-esters. The mixture is predominately mono-ester.

Further, the present invention relates to a method for enhancing the water solubility and stability of a salicylic acid and peroxide compound based aqueous skin cleanser comprising adding to said cleanser an effective amount of a phosphate ester, wherein said phosphate ester has one of the following structures:

Formula I

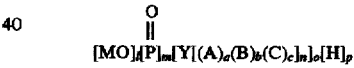

wherein $l=0-2.9$, $m=0.1-1$, $n=1$, $o=0.1-3$, $p=0-0.9$, A, B and C are ethylene oxide, propylene oxide, butylene oxide, tetramethylene oxide and mixtures thereof; $a=0-30$, $b=0-30$, $c=0-30$, M is H, alkali metal, or mixtures thereof; Y is a saturated or unsaturated, linear or branched, cyclic or acyclic, substituted or unsubstituted alcohol having from 1 to 30 carbon atoms;

or

Formula II

wherein $l=0-5.9$, $m=0.1-2$, $n=2$, $o=0.1-6$, $p=0-1.9$, A, B and C are ethylene oxide, propylene oxide, butylene oxide, tetramethylene oxide and mixtures thereof; $a=15-100$, $b=10-250$, $c=0-100$, M is H, alkali metal, or mixtures thereof; Y is a diol having from 2 to 30 carbon atoms, linear or branched, including but not limited to ethylene glycol, diethylene glycol, propylene glycol, and 1,10-decane diol or Y is an alkyl, aryl or alkylaryl primary amine including but not limited to tallow amine or aniline;

or

Formula III

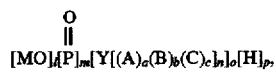

wherein l=0–8.9, m=0.1–3, n=3, o=0.1–9, p=0–2.9, A, B and G are ethylene oxide, propylene oxide, butylene oxide, tetramethylene oxide and mixtures thereof; a=15–120, b=10–350, c=100, M is H, alkali metal, or mixtures thereof; Y is the residue of an organic compound having three reactive hydrogens which are attached to oxygen, nitrogen or sulfur atoms and mixtures thereof;
or
Formula IV

wherein l=0–11.9, m=0.1–4, n=4, o=0.1–12, p=0–3.9, A, B and C are ethylene oxide, propylene oxide, butylene oxide, tetramethylene oxide and mixtures thereof; a=15–150, b=20–500, c=0–150, M is H, alkali metal, or mixtures thereof; Y is a tetrafunctional initiator containing reactive hydrogens attached to oxygen, nitrogen or sulfur atoms and mixtures thereof.

Each phosphate ester is a mixture of mono-, di- and tri-esters. The mixture is predominately mono-ester.

Preparation of the Skin Care Compositions of the Present Invention

The aqueous skin care compositions of the present invention are prepared according to methods known to those skilled in the art by blending peroxide compounds, salicylic acid, adjunct surfactants and phosphate esters in water.

Peroxides

Peroxides useful in the practice of the present invention include, but are not limited to, hydrogen peroxide, benzoyl peroxide, urea (carbamide) peroxide, zinc peroxide, sodium peroxide and any peroxide formed from organic peracids. These are obtainable from many sources. The preferred peroxides, useful for the present invention, include hydrogen peroxide, benzoyl peroxide and carbamide peroxide. Particularly preferred peroxides are hydrogen peroxide and benzoyl peroxide. Hydrogen Peroxide and benzoyl peroxide are obtainable from a variety of sources at varying concentrations. Hydrogen peroxide is typically available at a concentration of 30%. The peroxides are used at a preferred level of 0.5 to 5% by weight, a more preferred level of 0.5 to 3% by weight and a most preferred level of 1 to 2% by weight. Finally, blends of peroxides may be used in the compositions of the present invention.

Salicylic Acid

Salicylic acid is obtainable from a variety of sources. It is used at a preferred level of 0.5 to 5% by weight, a more preferred level of 0.5 to 3% by weight and a most preferred level of 1 to 2% by weight.

Adjunct Surfactants

Adjunct surfactants suitable for use in the skin care composition of the present invention, include, nonionic, anionic, and amphoteric.

Nonionic surfactants

Illustrative, but not limiting, examples of the various chemical types of suitable nonionic surfactants include:

(a) polyoxyalkylene (polyoxyethylene or polyoxypropylene) condensates of aliphatic carboxylic acids, whether linear or branched-chain and unsaturated or saturated, containing from about 8 to about 18 carbon atoms in the aliphatic chain and incorporating from 5 to about 50 ethylene oxide or propylene oxide units. Suitable carboxylic acids include "coconut" fatty acids (derived from coconut oil) which contain an average of about 12 carbon atoms, palmitic acid, myristic acid, stearic acid and lauric acid.

(b) polyoxyalkylene (polyoxyethylene or polyoxypropylene) condensates of aliphatic alcohols, whether linear- or branched- chain and unsaturated or saturated, containing from about 8 to about 24 carbon atoms and incorporating from about 3 to about 60 ethylene oxide or propylene oxide units. PLURAFAC® D 25 and A 39 surfactants are preferred polyoxyalkylene condensates of an aliphatic alcohol type surfactant which is available from BASF Corporation, Mt. Olive, N.J.

(c) polyoxyalkylene (polyoxyethylene or polyoxypropylene) condensates of alkyl phenols, whether linear- or branched- chain and unsaturated or saturated, containing from about 6 to about 12 carbon atoms and incorporating from about 5 to about 25 moles of ethylene oxide or propylene oxide.

(d) Particularly preferred nonionic surfactants are selected polyalkylene oxide block copolymers. This class can include polyethoxylated-polypropoxylated propylene glycol sold under the tradename "PLURONIC®" made by the BASF Corporation or polypropoxylated-polyethoxylated ethylene glycol sold under the tradename "PLURONIC-R®" made by the BASF Corporation, Mt. Olive, N.J. The first group of compounds are formed by condensing ethylene oxide with a hydrophobic base formed by the condensation of propylene oxide with propylene glycol (see U.S. Pat. No. 2,674,619). The hydrophobic portion of the molecule which, of course, exhibits water insolubility, has a molecular weight up to 3600. A preferred surfactant of the PLURONIC series is PLURONIC F 127. The latter series of compounds called "PLURONIC-R®" are formed by condensing propylene oxide with the polyethoxylated ethylene glycol condensate. This series of compounds is characterized by having an average molecular weight of about between 2000 and 9000 consisting of, by weight, from about 10 to 80 percent polyoxyethylene, and a polyoxypropylene portion having a molecular weight between about 1000 and 3100.

(e) sucrose and glucose ester non-ionic surfactants, sucrose and glucose amide non-ionic surfactants are also useful in the practice of the present invention for their reputed mildness to skin and hair.

U.S. Pat. Nos. 4,366,326; 4,624,803; 4,280,919; 4,340,766; 3,956,401; 5,200,236; 5,425,894; 5,294,365; incorporated by reference herein, describe in detail nonionic surfactants useful in the practice of this invention. *Surfactant Science Series*, edited by Martin J. Schick, Nonionic Surfactants, Vols. 19 and 23 provide detailed description of nonionic surfactants and are incorporated by reference herein. Finally, surfactant blends prepared from the surfactants described herein can be used in the practice of the present invention.

Anionic Surfactants

Useful anionic surfactants include the water-soluble salts, preferably the alkali metal, ammonium and substituted ammonium salts, of organic sulfuric acid reaction products having in their molecular structure of alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols ($C_8$–$C_{18}$ carbon atoms) such as those produced by reducing the glycerides of tallow or coconut oil; and the sodium and potassium alkylbenzenesulfonates in which the alkyl group contains from about 9 to about 15 carbon atoms in straight chain or branched chain configuration, e.g., those of the type described in U.S. Pat. Nos. 2,220,099 and 2,477,383 both of which are incorporated herein by reference. Especially valuable are linear straight chain alkylbenzene sulfonates in which the average number of carbon atoms in the alkyl group is from 11 to 13, abbreviated as $C_{11-13}$LAS.

Other anionic surfactants suitable for use herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and from about 8 to about 12 carbon atoms in the alkyl group; and sodium or potassium salts of alkyl ethylene oxide ether sulfates containing from about 1 to about 25 units of ethylene oxide per molecule and from about 10 to about 20 carbon atoms in the alkyl group.

Other useful anionic surfactants include the water-soluble salts of esters of alpha-sulfonated fatty acids containing from about 6 to 20 carbon atoms in the fatty acid group and from about 1 to 10 carbon atoms in the ester group; water-soluble salts of 2-acyloxy-alkane-1-sulfonic acids containing from about 9 to about 23 carbon atoms in the alkyl group and from about 8 to 20 carbon atoms in the moiety.

Particularly preferred surfactants herein are anionic surfactants selected from the group consisting of the alkali metal salts of $C_{11-13}$ alkylbenzene sulfonates, $C_{12-18}$ alkyl sulfates, $C_{12-18}$ alkyl linear polyethoxy sulfates containing from about 1 to about 10 moles of ethylene oxide, and mixtures thereof and nonionic surfactants that are the condensation products of alcohols having an alkyl group containing from about 9 to about 15 carbon atoms with from about 4 to about 12 moles of ethylene oxide per mole of alcohol.

Amphoteric Surfactants

Amphoteric surfactants, useful in the practice of the present invention, include derivatives of heterocyclic secondary and tertiary amines in which the aliphatic moiety can be straight chain or branched, and wherein one of the aliphatic substituents contains from about 8 to 18 carbon atoms and at least one aliphatic substituent contains an anionic water-solubilizing group.

The adjunct surfactants, nonionic, anionic and amphoteric, described hereinabove are used at a preferred level of 0.1 to 50% by weight; at a more preferred level of 5 to 30% by weight and at a most preferred level of 10 to 20% by weight.

Phosphate Esters

The phosphate esters useful in the skin and hair care compositions of the present invention are represented by Formula I, Formula II and Formula III and IV. Said skin and hair care compositions of the present invention may be comprised of Formula I, Formula II, Formula III, or Formula IV or mixtures of all four formulas.

Formula I

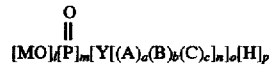

wherein l=0–2.9, m=0.1–1, n=1, o=0.1–3, p=0–0.9, A, B and C are ethylene oxide, propylene oxide, butylene oxide, tetramethylene oxide and mixtures thereof; a=0–30, b=0–30, c=0–30, M is H, alkali metal, or mixtures thereof; Y is a saturated or unsaturated, linear or branched, cyclic or acyclic, substituted or unsubstituted alcohol having from 1 to 30 carbon atoms.

Preferably, l=0–2.9, m=0.1–1, n=1, o=0.1–3, p=0–0.9.

More preferably, l=1–2.5, m=0.3–0.9, n=1, o=0.5–2.0, p=0.1–0.7.

Most Preferably, l=1.5–2.2, m=0.5–0.8 n=1, o=0.8–1.5, p=0.2–0.5

Preferably, a=0–30, b=0–30, c=0–30, Y=1–30

More preferably, a=5–20, b=0–15, c=0–15, Y=8–18

Most preferably, a=10–18, b=0–10, c=0–10, Y=10–14

The most preferred Formula I is KLEARFAC™ AA 270 wherein Y=a C10–12 alcohol with 2 moles PO and 13 moles EO added concurrently to yield a heteric oxide block reacted with polyphosphoric acid; b=0, c=0. KLEARFAC™ AA270 is available from the BASF Corporation, Mr. Olive, N.J.

or

Formula II

wherein l=0–5.9, m=0.1–2, n=2, o=0.1–6, p=0–1.9, A, B and C are ethylene oxide, propylene oxide, butylene oxide, tetramethylene oxide and mixtures thereof; a=15–100, b=10–250, c=0–100, M is H, alkali metal, or mixtures thereof; Y is a diol having from 2 to 30 carbon atoms, linear or branched, including but not limited to ethylene glycol, diethylene glycol, propylene glycol, and 1,10-decane diol or Y is an alkyl, aryl or alkylaryl primary amine including but not limited to tallow amine or aniline.

Preferably, l=0–5.9, m=0.1–2, n=2, 0=0.1–6, p=0–1.9

More Preferably, l=2–5.5, m=0.6–1.8, n=2, 0=0.5–4.0, p=0.2–1.4

Most preferably, l=3.5 to 5.1, m=1.0–1.6, n=2, 0=0.9–2.5, p=0.4–1.0

Preferably, a=15–100, b=10–250, c=0–100

More preferably, a=20–70, b=25–150, c=0–50

Most preferably, a=30–50, b=50–75, c=0–30

The most preferred Formula II is KLEARFAC™ 870, wherein Y=propylene glycol, b=62 and a=39, c=o, which is reacted with polyphosphoric acid. KLEARFAC™ 870 is available from the BASF Corporation, Mt. Olive, N.J.

or

Formula III

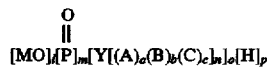

wherein l=0–8.9, m=0.1–3, n=3, o=0.1–9, p=0–2.9, A, B and C are ethylene oxide, propylene oxide, butylene oxide, tetramethylene oxide and mixtures thereof; a=15–120.

b=10–350, c=100, M is H, alkali metal, or mixtures thereof; Y is the residue of an organic compound having three reactive hydrogens which are attached to oxygen, nitrogen or sulfur atoms and mixtures thereof.

Preferably, l=0–8.9, m=0.1–3, n=3, o=0.1–9, p=0–2.9

More preferably, l=5.0–8.5, m=0.6–2.1, n=3, o=0.5–4.0, p=0.9–2.4

Most preferably, l=6.5–8.1, m=1.0–1.6, n=3, o=0.9–2.5 p=1.4–2.0

Preferably, a=15–120, b=10–350, c=0–100

More preferably, a=20–90, b=25–250, c=0–50

Most preferably, a=30–70, b=50–100, c=0–30 or

Formula IV

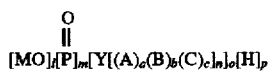

wherein l=0–11.9, m=0.1–4, n=4, o=0.1=12, p=0–3.9, A, B and C are ethylene oxide, propylene oxide, butylene oxide, tetramethylene oxide and mixtures thereof; a=15–150, b=20–500, c=0–150, M is H, alkali metal, or mixtures thereof; Y is a tetrafunctional initiator containing reactive hydrogens attached to oxygen, nitrogen or sulfur atoms and mixtures thereof.

Preferably, l=0–11.9, m=0.1–4, n=4, o=0.1–12, p=0–3.9

More preferably, l=6.0–11.5, m=0.5–2.5, n=4, o=0.4–6.0, p=1.5–3.5

Most preferably, l=8.5–11.1, m=1.0–2.0, n=4, o=0.9–3.5, p=2.0–3.0

Preferably, a=15–150, b=20–500, c=0–150

More Preferably, a=40–120, b=50–400, c=0–100

Most Preferably, a=60–100, b=100–350, c=0–60

Examples of Formula IV include, ethylene diamine, pentaerythritol, triethylene diamine, erythritol, hexamethylene diamine, phenylene diamine.

Each phosphate ester is a mixture of mono-, di- and tri-esters. The mixture is predominately mono-ester.

Other phosphate esters useful in the practice of the present invention include, but are not limited to, RHODAFAC™ PC100, PO3, and RA600 (available from Rhone-Pouloenc), and CRODAFOS™ N-3, N-10, N2A, N3A, N5A, and N10A (available from Croda).

Finally, the phosphate esters useful in the practice of the present invention are used at levels of 0.1–5% by weight, preferably 1–3% by weight.

Representative Skin Care Compositions of the Present Invention

The following non limiting Examples (I, II, III) represent the skin care compositions of the present invention (Table 1).

TABLE 1

|  | I | II | III |
|---|---|---|---|
| Deionized water | 65% w/w | 55% w/w | 69% w/w |
| PLURONIC ™ F127 (adjunct surfactant) | 25 | 25 | 25 |
| KLEARFAC ™ 870 (phos. Ester) | 1 | 1 | — |
| KLEARFAC ™ AA270 (phos. Ester) | — | — | 2 |
| Alkyl glucoside (adjunct surfactant) | 5 | 10 | — |
| Salicylic Acid | 2 | 2 | 2 |
| Hydrogen Peroxide | 2 | 2 | 2 |

We claim:

1. An aqueous skin care composition comprising:

a. 0.5 to 5% peroxides;
   b. 0.5 to 5% salicylic acid;
   c. 0.1 to 50% surfactant;
   d. 0.1 to 5% phosphate ester, selected from one of the following 4 structures or mixtures thereof:

Formula I

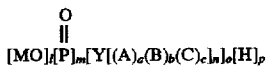

wherein l=0–2.9, m=0.1–1, n=1, o=0.1–3, p=0–0.9, A, B and C are ethylene oxide, propylene oxide, butylene oxide, tetramethylene oxide and mixtures thereof; a=0–30, b=0–30, c=0–30, M is H, alkali metal, or mixtures thereof; Y is a saturated or unsaturated, linear or branched, cyclic or acyclic, substituted or unsubstituted alcohol having from 1 to 30 carbon atoms;

or

Formula II

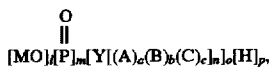

wherein l=0–5.9, m=0.1–2, n=2, o=0.1–6, p=0–1.9, A, B and C are ethylene oxide, propylene oxide, butylene oxide, tetramethylene oxide and mixtures thereof; a=15–100, b=10–250, c=0–100, M is H, alkali metal, or mixtures thereof; Y is a diol having from 2 to 30 carbon atoms, linear or branched, including but not limited to ethylene glycol, diethylene glycol, propylene glycol, and 1,10-decane diol or Y is an alkyl, aryl or alkylaryl primary amine including but not limited to tallow amine or aniline;

or

Formula III

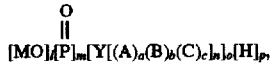

wherein l=0–8.9, m=0.1–3, n=3, o=0.1–9, p=0–2.9, A, B and C are ethylene oxide, propylene oxide, butylene oxide, tetramethylene oxide and mixtures thereof; a=15–120, b=10–350, c=100, M is H, alkali metal, or mixtures thereof; Y is the residue of an organic compound having three reactive hydrogens which are attached to oxygen, nitrogen or sulfur atoms and mixtures thereof;

or

Formula IV

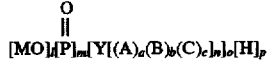

wherein l=0–11.9, m=0.1–4, n=4, o=0.1–12, p=0–3.9, A, B and C are ethylene oxide, propylene oxide, butylene oxide, tetrame thylene oxide and mixtures thereof; a=15–150, b=20–500, c=0–150, M is H, alkali metal, or mixtures thereof; Y is a tetrafunctional initiator containing reactive hydrogens attached to oxygen, nitrogen or sulfur atoms and mixtures thereof.

2. An aqueous skin care composition according to claim 1, wherein said phosphate ester (d) is Formula I and Y is a C10–12 alcohol with 2 moles PO and 13 moles EO added concurrently to yield a heteric oxide block reacted with polyphosphoric acid; and b=o; and c=o.

3. An aqueous skin care composition accoridng to claim 1, wherein said phosphate ester (d) is Formula II and Y=propylene glycol, b=62, and a=39; c=o.

4. An aqueous skin care composition according to claim 1, wherein said peroxide (a) is hydrogen peroxide.

5. An aqueous skin care composition according to claim 1, wherein said peroxide (a) is benzoyl peroxide.

6. A method for enhancing the water solubility and stability of a salicylic acid and peroxide based aqueous skin cleanser comprising adding to said cleanser an effective amount of a phosphate ester, wherein said phosphate ester is selected from one of the following 4 structures or mixtures thereof:

Formula I

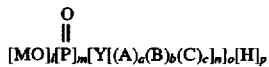

wherein l=0–2.9, m=0.1–1, n=1 o=0.1–3, p=0–0.9, A, B and C are ethylene oxide, propylene oxide, butylene oxide, tetramethylene oxide and mixtures thereof; a=0–30, b=0–30, c=0–30, M is H, alkali metal, or mixtures thereof; Y is a saturated or unsaturated, linear or branched, cyclic or acyclic, substituted or unsubstituted alcohol having from 1 to 30 carbon atoms;

or

Formula II

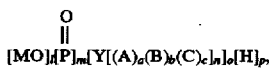

wherein l=0–5.9, m=0.1–2, n=2, o=0.1–6, p=0–1.9, A, B and C are ethylene oxide, propylene oxide, butylene oxide, tetramethylene oxide and mixtures thereof; a=15–100, b=10–250, c=0–100, M is H, alkali metal, or mixtures thereof; Y is a diol having from 2 to 30 carbon atoms, linear or branched, including but not limited to ethylene glycol, diethylene glycol, propylene glycol, and 1,10-decane diol or Y is an alkyl, aryl or alkylaryl primary amine including but not limited to tallow amine or aniline;

or

Formula III

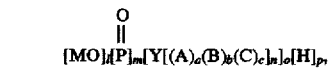

wherein l=0–8.9, m=0.1–3, n=3, o=0.1–9, p=0–2.9, A, B and C are ethylene oxide, propylene oxide, butylene oxide, tetramethylene oxide and mixtures thereof; a=15–120, b=10–350, c=100, M is H, alkali metal, or mixtures thereof; Y is the residue of an organic compound having three reactive hydrogens which are attached to oxygen, nitrogen or sulfur atoms and mixtures thereof;

or

Formula IV

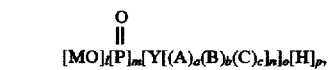

wherein l=0–11.9, m=0.1–4, n=4, o=0.1–12, p=0–3.9, A, B and C are ethylene oxide, propylene oxide, butylene oxide, tetramethylene oxide and mixtures thereof; a=15–150, b=20–500, c=0–150, M is H, alkali metal, or mixtures thereof; Y is a tetrafunctional initiator containing reactive hydrogens attached to oxygen, nitrogen or sulfur atoms and mixtures thereof.

7. A method according to claim 4, wherein said phosphate ester is Formula I and Y is C10–12 alcohol with 2 notes PO and 13 moles EO added concurrently to yield a heteric block reacted with polyphosphoric acid; and b=o; c=o.

8. A method according to claim 4, wherein said phosphate ester is Formula II and Y=propylene glycol, b=62, and a=39; c=o.

* * * * *